United States Patent [19]

Wilson, Jr.

[11] 4,067,933
[45] Jan. 10, 1978

[54] PHENOLIC PHOSPHITES AS STABILIZERS FOR POLYMERS

[75] Inventor: Farris H. Wilson, Jr., Cuyahoga Falls, Ohio

[73] Assignee: The Goodyear Tire & Rubber Company, Akron, Ohio

[21] Appl. No.: 650,588

[22] Filed: Jan. 19, 1976

Related U.S. Application Data

[62] Division of Ser. No. 405,247, Oct. 10, 1973, Pat. No. 3,959,221.

[51] Int. Cl.$^2$ ............................................. C07F 9/145
[52] U.S. Cl. .................................. 260/930; 260/2 P; 260/920; 260/953; 260/968; 260/982
[58] Field of Search .............. 260/2 P, 920, 930, 953, 260/982, 968

[56] References Cited

U.S. PATENT DOCUMENTS

| | | | |
|---|---|---|---|
| 3,297,631 | 1/1967 | Bown | 260/953 X |
| 3,361,846 | 1/1968 | Gleim | 260/953 X |
| 3,527,725 | 9/1970 | Strauss | 260/29.3 |

*Primary Examiner*—Richard L. Raymond
*Attorney, Agent, or Firm*—F. W. Brunner; J. A. Rozmajzl

[57] ABSTRACT

Polymers subject to oxidative degradation are stabilized by incorporating therein phosphite stabilizers such as the reaction product obtained by reacting a mixture of triphenylphosphite and 2,6-di-t-butyl-4-hydroxymethyl phenol or the reaction product obtained by reacting a mixture of triphenyl phosphite, 2,6-di-t-butyl phenol and paraformaldehyde.

8 Claims, No Drawings

PHENOLIC PHOSPHITES AS STABILIZERS FOR POLYMERS

This is a division of application Ser. No. 405,247, filed Oct. 10, 1973, which issued on May 25, 1976 as U.S. Pat. No. 3,959,221.

This invention relates to a new class of compounds and a process for making said compounds, these compounds having been found to possess unusual ability to stabilize polymers. More particularly, it is directed to a unique class of organic phosphites which are useful in stabilizing oxidizable polymers and a process for making said phosphites.

Phosphite stabilizers are well known in the art. However, the search for new and better phosphite stabilizers continues to command the attention of many skilled investigators. Most phosphite stabilizers offer very little protection to a vulcanized polymer if added prior to vulcanization. Phosphite stabilizers which offer some protection after vulcanization are highly desirable.

It is an object of this invention to provide a new class of organic phosphites that are particularly effective in stabilizing oxidizable polymers both vulcanized and unvulcanized. It is also an object of this invention to provide a process for making said phosphites. Other objects will become apparent as the description proceeds.

In accordance with the present invention, the foregoing and additional objects can be accomplished by employing as polymer stabilizers organic phosphites prepared by reacting a two component or a three component combination.

The two component combination comprises (A) a triaryl phosphite having the following structural formula

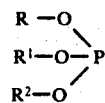

wherein R, $R^1$ and $R^2$ are selected from the group consisting of substituted (no more than two substituents) and unsubstituted aryl radicals having 6 to 20 carbon atoms, and (B) a hydroxy alkyl phenol having the following structural formula

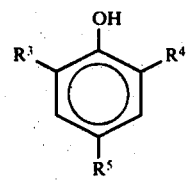

wherein $R^3$, $R^4$ and $R^5$ are selected from the group consisting of hydrogen, alkyl radicals having 1 to 12 carbon atoms, cycloalkyl radicals having 5 to 12 carbon atoms, aralkyl radicals having 6 to 12 carbon atoms and

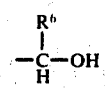

with at least one of $R^3$, $R^4$ and $R^5$ being

wherein $R^6$ is selected from the group consisting of hydrogen and alkyl radicals having 1 to 5 carbon atoms.

The three component combination comprises the reaction product prepared by reacting a combination comprising A. a triaryl phosphite having the following structural formula

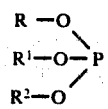

wherein R, $R^1$ and $R^2$ are selected from the group consisting of substituted and unsubstituted aryl radicals having 6 to 20 carbon atoms, B. a phenol selected from the group consisting of phenols having the following structural formulae

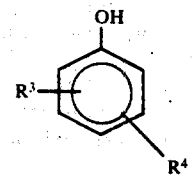

wherein $R^3$ and $R^4$ are selected from the group consisting of hydrogen, alkyl radicals having 1 to 12 carbon atoms, cycloalkyl radicals having 5 to 12 carbon atoms and aralkyl radicals having 6 to 12 carbon atoms, and C. an aldehyde having the following structural formula

R — CHO where R is selected from the group consisting of hydrogen and alkyl radicals having 1 to 10 carbon atoms.

In both the two and three component combinations R, $R^1$ and $R^2$ are preferably selected from the group consisting of phenyl, alkyl phenyl and alkyl thio phenyl radicals where the alkyl radical is a straight chain or branched chain radical having 1 to 20 carbon atoms, e.g., nonyl.

Representative examples of phosphite reactants used in the practice of the present invention are listed below.

Tris phenyl phosphite
Tris(methyl phenyl) phosphite
Tris(butyl phenyl) phosphite
Tris(nonyl phenyl) phosphite
Tris(methyl thiophenyl) phosphite
Tris(ethyl thiophenyl) phosphite
Tris(propyl thiophenyl) phosphite
Tris(butyl thiophenyl) phosphite
Tris(octyl thiophenyl) phosphite
Tris(dibutyl phenyl) phosphite
Tris(dimethyl phenyl) phosphite In the two component reaction the preferred phenolic reactants are those where at least one of $R^3$ and $R^4$ is a tertiary alkyl radical having 4 to 8 carbon atoms. Preferably $R^6$ is hydrogen or methyl. Preferred embodiments include those where both $R^3$ and $R^4$ are tertiary alkyl groups having 4 to 8 carbon atoms and $R^5$ is

and where $R^3$ is a tertiary alkyl group containing 4 to 8 carbon atoms, $R^5$ is methyl and $R^4$ is

In the two component reaction the following phenolic compounds are illustrative of the phenolic reactants that can be used.

2,6-di-t-butyl-4-hydroxymethyl phenol
2,4-di-t-butyl-6-hydroxymethyl phenol
2,4-dihydroxymethyl-6-methyl phenol
2-butyl-4-methyl-6-hydroxymethyl phenol
2,6-dihexyl-4-hydroxymethyl phenol
2,4-dihexyl-6-hydroxymethyl phenol
2,4-dihydroxymethyl-6-butyl phenol
2-hexyl-4-methyl-6-hydroxymethyl phenol
2,6-dioctyl-4-hydroxymethyl phenol
2,4-dioctyl-6-hydroxymethyl phenol
2,4-dihydroxymethyl-6-octyl phenol
2-butyl-4-octyl-6-hydroxymethyl phenol In the three component reaction the preferred phenolic reactants are those where at least one of $R^3$ and $R^4$ is a tertiary alkyl radical having 4 to 8 carbon atoms. Preferably $R^3$ and $R^4$ are in either ortho or para positions.

In the three component reaction the following phenolic compounds are illustrative of the phenolic reactants that can be used.

2-butyl phenol
4-butyl phenol
2,4-dibutyl phenol
2,6-dibutyl phenol
2-hexyl phenol
4-hexyl phenol
2,4-dihexyl phenol
2,6-dihexyl phenol
2-octyl phenol
4-octyl phenol
2,4-dioctyl phenol
2,6-dioctyl phenol
2-butyl-4-methyl phenol
2-hexyl-4-methyl phenol
2-octyl-4-methyl phenol
2-nonyl phenol
4-nonyl phenol The alkyl substituents of these phenolic reactants can be normal, secondary or tertiary.

Aldehydes which are illustrative of those used in the three component reaction are formaldehyde, acetaldehyde, propionaldehyde and butyraldehyde.

The two and three component systems are reacted in the following general manner. The order of addition of the reactants is not critical. Generally all of the components are added at the beginning of the reaction. A solvent is normally unnecessary. In fact, in one instance when toluene was used as a solvent, the reaction did not occur. In the two step process the molar ratio of the phosphite to the phenolic reactant can be from about 1:1 to 1:9, preferably from about 1:2 to 1:4. In the three step process the molar ratio of the phosphite to the aldehyde to the phenolic reactant can be from about 1:1:1 to 1:9:9, preferably from 1:2:2 to 1:4:4. A general procedure is to charge the compounds together, place the combination under a vacuum of about 15 mm. of Hg., and commence heating. Generally between about 45° C. and 80° C. an exothermic reaction begins, and if not controlled temperatures may rise to as high as 150° C. to 160° C. Generally it is desirable to control the temperatures to a range of about 100° C. to 125° C.

Since the reactions involving the two and three component systems are condensation reactions they can be catalyzed by any of the well known acidic condensation catalysts represented by sulfuric acid, hydrochloric acid, phosphoric acid, toluene sulfonic acid, oxalic acid and acetic acid. The type of acidic condensation catalyst is not critical to the practice of this invention. In fact, although always preferred, a catalyst is not even necessary for the condensation reactions involving the two component system and for some of the embodiments of the three component system.

The phosphites used in the two and three component combinations are well known in the art as is their method of preparation. Generally they are prepared by reacting phosphorous trichloride with a phenolic compound, although well known transesterification reactions may sometimes be used.

The α-hydroxy alkyl phenols used in the two component system can be prepared by the reaction of an aldehyde with a phenol using a basic catalyst. Generally if more than one ortho or para position is unsubstituted on the phenolic compound, the yield of the α-hydroxy alkyl phenols will be reduced because of the formation of alkylidene bisphenols.

The other phenolic compounds and the aldehydes used as reactants, as well as their methods of preparation, are all extremely well known in the art.

The following examples 1 to 5 are presented as illustrations of the preparation of typical organic phosphites of the present invention, but are not to be construed as limiting the scope of the invention.

EXAMPLE 1

Fifty grams of triphenylphosphite, 125 grams of 2,6-di-t-butyl-6-hydroxymethyl phenol and 3 grams of sodium hydroxide were charged to a flask and warmed under vacuum to about 45° C. An exothermic reaction began and temperature rose to 137° C. Some distillate began to form. When the temperature dropped to 120° C. heating was begun and gradually raised to 190° C. Ten grams of material was collected in the receiver. There remained 144 grams of crude product in the pot. The melting point of the mixture was 60° C. to 95° C. The product was a white resinous material.

EXAMPLE 2

Fifty grams of triphenylphosphite and 42 grams of 2,6-di-t-butyl-4-hydroxymethyl phenol were charged to a flask and warmed to 45° C. under vacuum. An exothermic reaction raised the temperature to 110° C. When the temperature began to drop, heating was begun and gradually raised to 150° C. at 10 mm. Hg. Twelve grams of distillate were collected. There remained 79 grams of a sticky semi-solid product in the pot.

EXAMPLE 3

Fifty-two grams of triphenylphosphite, 103 grams of 2,6-di-t-butyl phenol, 16.5 grams of paraformaldehyde and 1.5 grams of toluene sulfonic acid were charged to a flask with the acid being added last. A vacuum of 11 mm. Hg. was pulled and heating begun. The temperature was gradually raised to 95° C. over a 5 hour period with some indications of reaction. The reaction mixture was stripped up to 137° C. pot temperature at 25 mm. Hg. There remained 158 grams of product.

EXAMPLE 4

One hundred thirty grams of o-tert-butyl-p-cresol, 75 grams of triphenyl phosphite, 25 grams of paraformaldehyde and 1 gram of toluene sulfonic acid were charged to a flask and a 13 mm. Hg. vacuum was drawn. Heating was begun and at about 60° C. an exothermic reaction raised the temperature to 108° C. even with cooling. After heating 7 hours at 70° C., 200 ml. of toluene and 2 grams of sodium carbonate were added. The mixture was digested 1 hour at 70° C., filtered and stripped to 120° C. pot temperature at 15 mm. Hg. There remained 220 grams of a cloudy viscous liquid product.

EXAMPLE 5

One hundred thirty grams of o-tert-butyl-p-cresol, 75 grams of triphenyl phosphite and 37 grams of paracetaldehyde were charged to a 1 liter flask equipped with stirrer, thermometer and a short column leading to a distilling head and receiver. The reaction was heated to 30° C. and practically all of the cresol had gone into solution. One gram of toluene sulfonic acid was added and the temperature began to rise. It rose to 74° C. over a period of 25 minutes and then began to drop. Heating was begun and a vacuum pulled on the system. The mixture was heated to 103° C. under a 15 mm. Hg. vacuum over a period of 1.5 hours. It was allowed to cool to 50° C. under vacuum. There remained 228 grams of product.

The polymers that may be conveniently protected by the compounds described herein are oxidizable vulcanized and unvulcanized polymers susceptible to oxygen degradation, such as natural rubber, balata, gutta percha and oxidizable synthetic polymers including those containing carbon to carbon double bonds, such as rubbery diene polymers. Representative examples of the synthetic polymers used in the practice of this invention are polychloroprene; homopolymers of a conjugated 1,3-diene such as isoprene and butadiene, and in particular, polyisoprenes and polybutadienes having essentially all of their repeat units combined in a cis-1,4 structure; copolymers of a conjugated 1,3-diene such as isoprene and butadiene with up to 50 percent by weight of at least one copolymerizable monomer including ethylenically unsaturated monomers such as styrene and acrylonitrile; butyl rubber, which is a polymerization product of a major proportion of a monoolefin and a minor proportion of a multiolefin such as butadiene or isoprene; polyurethanes containing carbon to carbon double bonds; and polymers and copolymers of monoolefins containing little or no unsaturation, such as polyethylene, polypropylene, ethylene propylene copolymers and terpolymers of ethylene, propylene and a nonconjugated diene such as dicyclopentadiene, 1,4-hexadiene, ethylidene norbornene and methylene norbornene.

The organic phosphite stabilizers of this invention may be used with or without other stabilizers, vulcanizing agents, accelerators or other compounding ingredients. In order to effectively stabilize polymers, small proportions of one or more of the organic phosphites in accordance with this invention are added to the polymer in a customary antioxidant amount which may vary somewhat depending upon the type and requirements of the polymers to be produced. The compounds of this invention are useful in protecting polymer in any form, for example, polymer in latex form, unvulcanized polymer and vulcanized polymer. The phosphite stabilizers of the present invention offer an advantage over many of the prior art stabilizers in that they offer antioxidant protection to a vulcanized polymer even though they are added to the polymer prior to vulcanization. This is due to the fact that they have a phenolic portion capable of offering antioxidant protection.

The method of addition of the antioxidant to the polymer is not critical. It may be added by any of the conventional means such as by adding to a polymer latex, milling on an open mill or by internal mixing. When the stabilizers of this invention are employed to stabilize the cis-1,4 polyisoprene or cis-1,4 polybutadiene rubbers as described above, a convenient method or incorporation consists of adding the stabilizers to the inert organic solvent in which these polymers are normally prepared after the polymerization of the monomers is essentially complete. Normally from about 0.001 part to about 5.0 parts of the antioxidant by weight based on the weight of the polymer can be used, although the precise amount of these effective stabilizers which is to be employed will depend somewhat on the nature of the polymer and the severity of the deteriorating conditions to which the polymer is to be exposed. In unsaturated polymers such as those made from conjugated dienes, e.g., rubbery butadiene/styrene polymers, the amount of antioxidant necessary is greater than that required by saturated polymers such as polyethylene. It has been found than an effective antioxidant amount of the disclosed stabilizer in polymers will generally range from about 0.05 part to about 5.0 parts by weight or higher based on 100 parts by weight of the polymer although it is commonly preferred to use from about 0.5 part to about 2.0 parts by weight based on 100 parts by weight of the polymer in most instances.

The following examples are intended to illustrate but not to be limiting as to the useage of the phosphite stabilizers of the present invention in oxidizable polymers. Unless otherwise indicated all parts are parts by weight.

One part of the stabilizers shown in the following table were added to 100 parts of SBR polymer. Unstabilized SBR-1006 (a hot styrene/butadiene rubber), which was prepared in the form of a latex and coagulated with isopropyl alcohol, was dissolved in benzene to form a cement. The stabilizers were added to portions of the cement containing three percent rubber in amounts sufficient to provide one part of antioxidant per 100 parts of rubber. The cements were cast onto aluminum foil sheets, 4 × 6 inches, and after evaporation of the benzene there remained a thin film adhering to the foil. The weight of the film was determined and the foil with the adhering film was placed in the oxygen absorption apparatus. The time required for each sample to absorb 1.0 percent oxygen was determined and recorded in the following table.

This testing procedure is described in further detail in Industrial and Engineering Chemistry 43, p. 456 (1951) and Industrial and Engineering Chemistry 45, p. 392 (1953).

| Antioxidant | Hours to 1% $O_2$ |
|---|---|
| Series A | |
| 2,6-di-t-butyl-4-hydroxymethylphenol | 303 |
| Example 1 | 428 |
| Example 2 | 514 |
| Series B | |
| Triphenyl phosphite | 35 |
| Example 3 | 341 |
| Series C | |
| Wing-Stay L* | 272 |
| Example 4 | 439 |
| Series D | |
| Example 5 | 423 |
| Wing-Stay L* | 384 |

*Trademark of the Goodyear Tire & Rubber Company - a phenolic antioxidant.

Various other antioxidants (1.0 part by weight per 100 parts of rubber) of the invention were tested in a butadiene/styrene rubber. The results are listed in the table below, the products being identified by the reactants and molar ratios.

| Two Component System | | | |
|---|---|---|---|
| Phosphite | Phenol | Molar Ratio | Oxygen[1] Absorption |
| Triphenyl phosphite | 2,6-di(hydroxymethyl)-p-cresol | 1/1.85 | 65.4 |
| Tris(nonylphenyl) phosphite | " | 1/3.22 | 121.8 |
| Triphenyl phosphite | " | 1/6 | 140 |
| Triphenyl phosphite | " | 1/9 | 144 |
| Tris[4(methylthio)phenyl]phosphite | " | 1/3 | 145 |
| Triphenyl phosphite | " | 1/4 | 145.5 |
| " | " | 1/2 | 154 |
| " | " | 1/4 | 157 |
| " | " | 1/1 | 165 |
| " | " | 1/3 | 198 |

[1]$100 \times \frac{\text{Hours to 1.0\% oxygen absorption of reaction product}}{\text{Hours to 1.0\% oxygen absorption of Wing-Stay L}}$ The time to 1% oxygen absorption for rubber with no antioxidant or stabilizer is 2.4% of that for Wing-Stay L.

| Three Component System | | | | |
|---|---|---|---|---|
| Phosphite | Phenol | Aldehyde | Molar Ratio | $O_2$[1] Abs. |
| Triphenyl Phosphite | mono styryl phenol | formaldehyde | 1/1.78/3.23 | 74.3 |
| " | nonyl phenol | " | 1/3/3 | 100 |
| " | 2,6-di-t-butyl phenol | " | 1/3/3.3 | 120 |
| " | " | " | 1/5.5/3.24 | 163.9 |
| " | o-t-butyl-p-cresol | " | 1/3.3/3.45 | 193 |
| " | " | " | 1/3.3/3.3 | 198 |

[1]$100 \times \frac{\text{hours to 1.0\% oxygen absorption of reaction product}}{\text{hours to 1.0\% oxygen absorption of Wing-Stay L}}$ Polypropylene has also been stabilized effectively with antioxidants of the present invention.

As indicated by the above data, the phosphites of the present invention offer quite effective protection against oxidative degradation. If the polymers were vulcanized, they would still be provided with measurable protection.

Any of the previously described reactants could be used as described earlier herein to prepare phosphite antioxidants which could be substituted for the phosphite stabilizers in the above working examples to effectively stabilize the polymer. Likewise the other polymers described herein could be substituted for the polymers of the working examples and be effectively stabilized.

Although many phenolic and phosphite type antioxidants possess color properties superior to the phenolic phosphites of the present invention, the antioxidants of the present invention do have color properties superior to other antioxidants such as phenyl-$\beta$-naphthylamine or N,N'-diphenyl-p-phenylenediamine.

The present invention may be advantageously employed in the manufacture of polymer which is to be used for making a wide variety of articles including tires, tubes shoes, all types of light-colored rubber articles, hose, coating compositions, etc.

The substituents that can be present on the aryl (e.g., phenyl) groups for R, $R^1$ and $R^2$ include the chloro radical and aralkyl radicals having 7 to 20 carbon atoms (e.g., $\alpha$-phenethyl). Some of the phosphites and a method of preparation are revealed in U.S. Pat. No. 2,733,226.

The general effect of catalysts on reactions between phenolics and formaldehyde are revealed in the text, *Phenolic Resins*, A. A. K. Whitehouse, E. G. K. Pritchett and G. Barnett, American Elsevier Publishing Company, Inc. (1967) page 7.

The R, $R^1$ and $R^2$ aryl radicals in the triaryl phosphite reactants described herein, when substituted, do not contain more than two substituents, whether used in the one or two component reaction combinations. For example, the aryl groups can contain none, one or two substituents such as alkyl and alkylthio substituents where the alkyl contains 1 to 20 carbon atoms, the chloro radical and aralkyl radicals having 7 to 20 carbon atoms such as benzyl and $\alpha$-phenethyl.

All of the alkyl radicals described generally or specifically herein, whether part of the phenolic, phosphite or aldehyde reactants are intended to include all of the isomeric forms thereof, e.g., normal, secondary, and tertiary alkyl groups. For example, the tris(butyl thiophenyl) phosphite recited earlier herein is intended to include n-butyl, sec-butyl, iso-butyl and tert.butyl radicals.

While certain representative embodiments and details have been shown for the purpose of illustrating the invention, it will be apparent to those skilled in this art that various changes and modifications may be made therein without departing from the spirit or scope of the invention.

I claim:

1. A composition prepared by reacting a combination comprising (A) a triaryl phosphite having the following structural formula

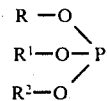

wherein R, $R^1$ and $R^2$ are selected from the group consisting of phenyl and substituted phenyl wherein the substituted phenyl contains one or two substituents selected from the group consisting of alkyl radicals containing 1 to 20 carbon atoms, alkylthio radicals containing 1 to 20 carbon atoms, chloro and aralkyl radicals having 7 to 20 carbon atoms, and (B) a hydroxy alkyl phenol having the following structural formula

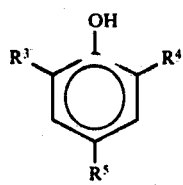

wherein $R^3$, $R^4$ and $R^5$ are selected from the group consisting of hydrogen, alkyl radicals having 1 to 12 carbon atoms, cycloalkyl radicals having 5 to 12 carbon atoms, aralkyl radicals having 6 to 12 carbon atoms and

with at least one of $R^3$, $R^4$ and $R^5$ being

and wherein at least one of $R^3$ and $R^4$ is a tertiary alkyl radical having 4 to 8 carbon atoms, wherein $R^6$ is selected from the group consisting of hydrogen and alkyl radicals having 1 to 5 carbon atoms, wherein the molar ratio of the phosphite reactant to the phenolic reactant is from 1:1 to 1:9.

2. The composition of claim 1 wherein R, $R^1$ and $R^2$ are selected from the group consisting of phenyl, alkyl phenol and alkyl thio phenyl radicals where the alkyl radical contains 1 to 20 carbon atoms and $R^6$ is selected from the group consisting of hydrogen and methyl.

3. The composition of claim 2 where both $R^3$ and $R^4$ are tertiary alkyl groups having 4 to 8 carbon atoms and $R^5$ is

4. The composition of claim 1 where $R^3$ is a tertiary alkyl group containing 4 to 8 carbon atoms, $R^5$ is methyl and $R^4$ is

5. The composition of claim 1 wherein the triaryl phosphite is tris phenyl phosphite and the hydroxy alkyl phenol is 3,5-di.tert.butyl-4-hydroxybenzylalcohol.

6. A composition prepared by reacting a combination comprising
A. a triaryl phosphite having the following structural formula

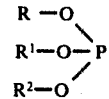

wherein R, $R^1$ and $R^2$ are selected from the group consisting of phenyl and substituted phenyl wherein the substituted phenyl contains one or two substituents selected from the group consisting of alkyl radicals containing 1 to 20 carbon atoms, alkylthio radicals containing 1 to 20 carbon atoms, chloro and aralkyl radicals having 7 to 20 carbon atoms,
B. a phenol selected from the group consisting of phenols having the following structural formulae

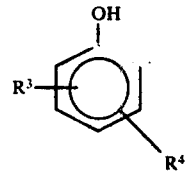

wherein $R^3$ and $R^4$ are selected from the group consisting of hydrogen, alkyl radicals having 1 to 12 carbon atoms, cycloalkyl radicals having 5 to 12 carbon atoms and aralkyl radicals having 6 to 12 carbon atoms and wherein at least one of $R^3$ and $R^4$ is a tertiary alkyl radical having 4 to 8 carbon atoms and is in a position ortho to the phenolic hydroxy group, and
C. an aldehyde having the following structural formula

R — CHO where R is selected from the group consisting of hydrogen and alkyl radicals having 1 to 10 carbon atoms, wherein the molar ratio of phosphite/aldehyde/phenolic reactant is from 1:1:1 to 1:9:9.

7. The composition of claim 6 wherein R, $R^1$ and $R^2$ are selected from the group consisting of phenyl, alkyl phenyl and alkyl thio phenyl radicals where the alkyl radical is a straight chain or branched chain radical having 1 to 20 carbon atoms and $R^6$ is selected from the group consisting of hydrogen and methyl.

8. The composition of claim 6 wherein the triaryl phosphite is tris phenyl phosphite, the phenol is o-tert.butyl-p-cresol and the aldehyde is formaldehyde.

* * * * *